United States Patent [19]

Holzwarth et al.

[11] Patent Number: 5,127,518

[45] Date of Patent: Jul. 7, 1992

[54] PACKAGE FOR SURGICAL SUTURES

[75] Inventors: Henry A. Holzwarth, Weston; Christopher M. Scanlon, Milford, both of Conn.

[73] Assignee: United States Surgical Corporation, Norwalk, Conn.

[21] Appl. No.: 697,757

[22] Filed: May 9, 1991

[51] Int. Cl.⁵ .................... A61B 17/06; B65B 11/00; B65B 7/00
[52] U.S. Cl. .................... 206/63.3; 53/461; 53/476
[58] Field of Search .................... 206/63.3; 53/476, 461

[56] References Cited

U.S. PATENT DOCUMENTS

| 268.811 | 5/1893 | Black |  |
|---|---|---|---|
| 2,332,412 | 10/1943 | Taylor | 206/491 X |
| 2,399,000 | 4/1946 | Carroll | 206/438 X |
| 2,415,151 | 2/1947 | Taylor | 206/491 X |
| 2,617,523 | 11/1952 | Zoller | 206/63.3 |
| 2,692,676 | 10/1954 | Grover | 206/63.3 |
| 3,037,619 | 6/1962 | Stevans | 206/63.3 |
| 3,136,418 | 6/1964 | Stacy et al. | 206/63.3 |
| 3,363,751 | 1/1968 | Shave et al. | 206/63.3 |
| 3,444,994 | 5/1969 | Kaepernik et al. | 206/63.3 |
| 3,487,917 | 1/1970 | Shave et al. | 206/63.3 |
| 3,568,883 | 3/1971 | Reynolds | 206/438 X |
| 3,939,969 | 2/1976 | Miller et al. | 206/63.3 |
| 3,951,261 | 4/1976 | Mandel et al. | 206/227 |
| 3,985,227 | 10/1976 | Thyen et al. | 206/63.3 |
| 4,014,434 | 3/1977 | Thyen | 206/63.3 |
| 4,120,395 | 10/1978 | Mandel et al. | 206/63.3 |
| 4,121,711 | 10/1978 | Bolanowski | 206/63.3 |
| 4,135,623 | 1/1979 | Thyen | 206/63.3 |
| 4,239,104 | 12/1980 | Roccaforte et al. | 206/335 X |
| 4,249,656 | 2/1981 | Cerwin et al. | 206/63.3 |
| 4,253,563 | 3/1981 | Komarnycky | 206/63.3 |
| 4,284,194 | 8/1981 | Flatau | 206/63.3 |
| 4,406,363 | 9/1983 | Aday | 206/63.3 |
| 4,412,613 | 11/1983 | Kubas | 206/63.3 |
| 4,412,614 | 11/1983 | Ivanov et al. | 206/63.3 |
| 4,413,727 | 11/1983 | Cerwin et al. | 206/63.3 |
| 4,483,437 | 11/1984 | Cerwin et al. | 206/63.3 |
| 4,491,218 | 1/1985 | Aday | 206/63.3 |
| 4,496,045 | 1/1985 | Ferguson et al. | 206/63.3 |
| 4,533,041 | 8/1965 | Aday et al. | 206/63.3 |
| 4,555,016 | 11/1985 | Aday et al. | 206/63.3 |
| 4,574,948 | 3/1986 | Huck et al. | 206/63.3 |
| 4,574,957 | 3/1986 | Stead | 206/63.3 |
| 4,615,435 | 10/1986 | Alpern et al. | 206/63.3 |
| 4,884,681 | 12/1989 | Roshdy et al. | 206/63.3 |
| 4,887,710 | 12/1989 | Roshdy et al. | 206/63.3 |
| 4,896,767 | 1/1990 | Pinheiro | 206/63.3 |
| 4,946,043 | 8/1990 | Roshdy et al. | 206/63.3 |

Primary Examiner—William I. Price
Attorney, Agent, or Firm—Thomas R. Bremer; Peter G. Dilworth; Rocco S. Barrese

[57] ABSTRACT

A package for surgical sutures and suture-needle assemblies which includes a series of panels foldable about each other to enclose the sutures in an unfolded and elongated condition.

39 Claims, 6 Drawing Sheets

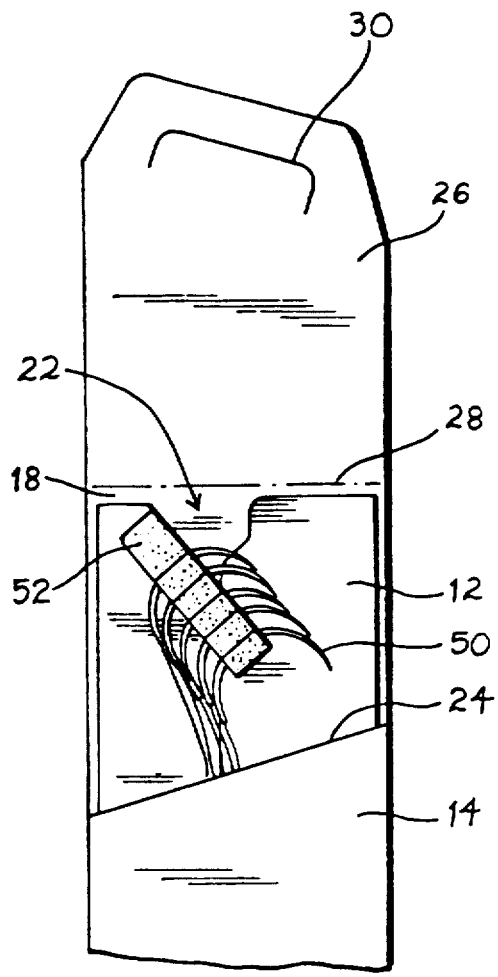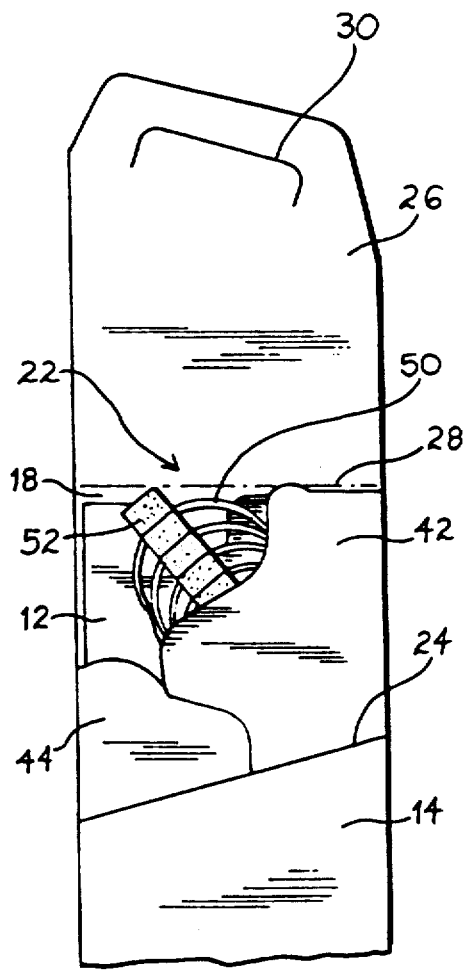
FIG.5  FIG.6
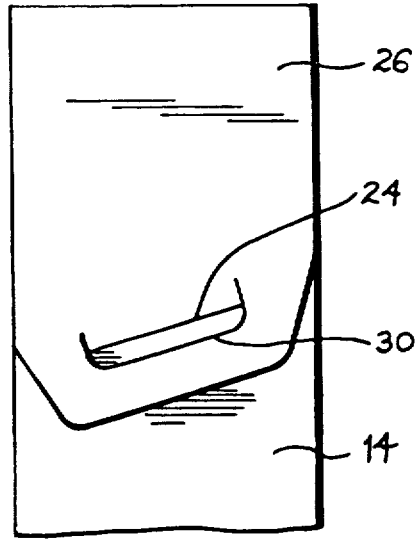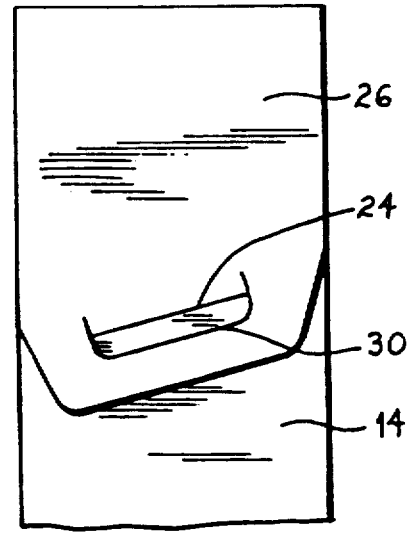
FIG.7  FIG.8

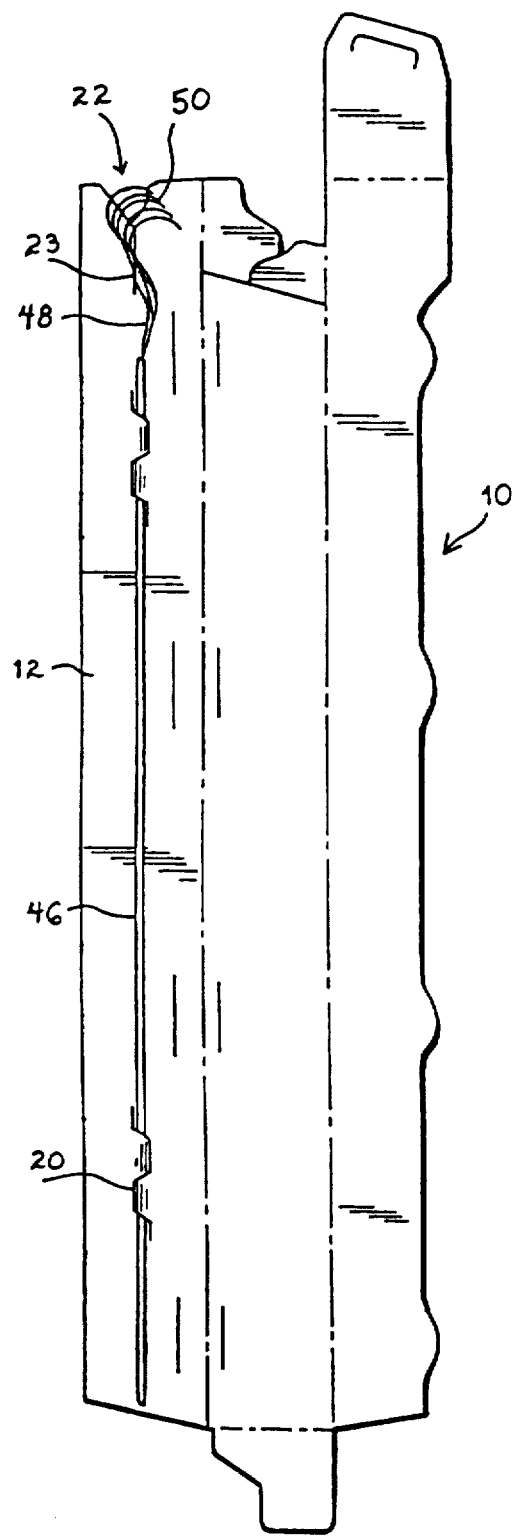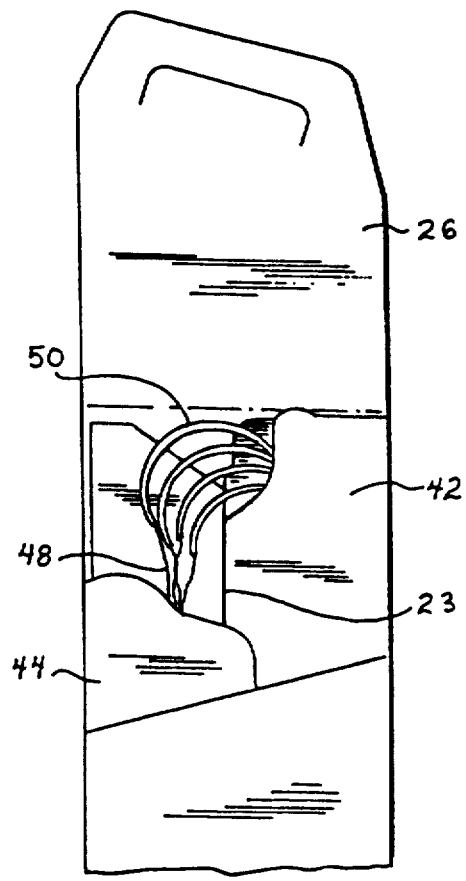
FIG. 9
FIG. 10

PACKAGE FOR SURGICAL SUTURES

CROSS-REFERENCE TO RELATED APPLICATIONS

This application is a continuation-in-part of copending U.S. application Ser. No. 07/637,186, filed Jan. 3, 1991 and now abandoned.

BACKGROUND OF THE INVENTION

1. Field of the Invention

The present invention relates to packaging devices for surgical elements such as sutures and suture-needle assemblies, and more particularly to packages for monofilament-type sutures which are packaged in an unfolded and elongated condition.

2. Discussion of the Prior Art

Packages for surgical sutures and suture-needle assemblies having means for retaining the suture in the package are well known in the art. These packages typically provide a series of panels which are foldable about each other to enclose the suture within. In most cases, means are provided on the package for securing the needle in place, positioning the suture within the package where the suture is restrained from moving once the package is closed.

In general, most suture packages in the prior art provide a retainer member consisting of a series of panels having perforated score lines which allow one panel to fold over another panel to close the retainer with the suture and needle packaged therein. Typically, the suture is wound in an oval or figure "8" pattern which reduces the size of the package and provides an efficient means for storing the sutures prior to use. Other packages provide a series of elongated loops which allows the suture to be stored in a relatively flattened condition with only a few bends in the suture material.

In the surgical suture and suture-needle industry, a significant amount of emphasis has recently been placed on the condition of the suture when it is removed from the package. The "memory" retention of the suture has become an important feature in the practical use of sutures in an operating room, in that emphasis has been placed on the necessity of sutures having little or no bends or creases after they are removed from the package. In general, sutures that are wound in small packages in a figure "8" or oval pattern will exhibit numerous bends and creases along their length after they are removed from the package. This leads to an awkward suturing and stitching process in the operating room, in that the operating room personnel must first straighten the suture material to assist the surgeon in the process. Furthermore, the bends and creases may lead to entanglement of the sutures, particularly in packages in which numerous sutures are enclosed.

Several types of sutures are prone to bending and creasing and as a result require packaging in individual paths or tracks within the suture package, which often leads to an expensive and elaborate package requiring additional assembly steps during manufacture. In particular, sutures constructed of plastic material such as polypropylene or sutures constructed of stainless steel easily develop creases during packaging which reduce the effectiveness of the suture in an operating room. Accordingly, it is important that these types of sutures be packaged with a minimal amount of bends or turns, in order to allow the suture to maintain its natural shape after removal from the package.

While some packages in the prior art provide for the suture to be packaged in an elongated condition, these packages require at least one turn or bend in the suture to secure the suture within the package, particularly in cases where the suture is a "double-armed" suture, having needles at both ends of the suture. The bend in suture packaged in this manner is usually a sharp, 180° turn, which usually remains in the suture after the suture is removed from the package.

The novel package for surgical sutures and suture-needle assemblies of the present invention obviates the disadvantages encountered in the prior art and provides a package which eliminates folds and creases in the suture material, which results in an elongated suture which maintains its natural shape after the suture has been removed from the package.

SUMMARY OF THE INVENTION

The present invention provides a novel package for surgical sutures and suture-needle assemblies which allows the suture to maintain its natural shape during packaging as well as after the suture is removed from the package for use in an operating room. The package is particularly suited for use with sutures that easily crease upon bending, such as sutures constructed of plastic material (for instance, polypropylene) or stainless steel.

The package of the present invention essentially comprises a sheet of packaging material such as paperboard, fiberboard, or any fibrous material such as Tyvek (a registered trademark of DuPont), which is die cut to form a series of interconnected panels. Preferably, the package of the present invention comprises three panels which are connected through scored or perforated lines which facilitate folding of the material about itself to form a package. A first panel is provided with means for securing the suture and suture-needle assembly in an elongated and unfolded condition. The means for securing the sutures comprises an elongated tubular member, preferably constructed of plastic or a rolled paperboard material which provides a tubular housing for the sutures which essentially eliminates the possibility of bending or creasing of the suture material. The tubular member is secured to &:he first panel of the package in a series of overlapping die cuts in the material which allows the material to grasp the tubular member to hold it in place. Alternately, an adhesive material or glue may be used to secure the tube to the first panel. The first panel may also be provided with a needle-retaining member, preferably a foam, adhesive-backed needle park which holds the needles in place within the package.

The second panel, which forms the front panel of the package, is provided with a bottom flap which folds over to form a bottom of the package, and may also be provided with a needle display means adjacent the needles which allows the needles to be covered within the package when the package is closed, and facilitates display and removal of the needles from the package without having to fully open the package to remove the sutures and needles.

The third panel forms the back panel of the package and is provided with a top extension flap which folds over the top of the package to completely enclose the needles. The third panel is also provided with means for holding the package in a closed position, where the third panel cooperates with the first panel to maintain the package in a folded, closed condition. The locking means generally comprises a tab and slot arrangement, but may also include adhesives such as heat activated adhesives to seal the third panel to the first panel to close the package. The tab may extend outwardly from the longitudinal edge of the third panel, but preferably is an inwardly die-cut tab, so that the longitudinal edge of the third panel is straight.

BRIEF DESCRIPTION OF THE DRAWINGS

The foregoing features of the present invention will become more readily apparent and may be understood by referring to the following detailed description of an illustrative embodiment of the package for surgical sutures and suture-needle assemblies and its novel construction, taken in conjunction with the accompanying drawings, in which:

FIG. 5 illustrates a partial perspective view of the surgical suture and suture-needle assembly package of FIG. 3 in the folded condition showing the needles exposed;

FIG. 6 illustrates a partial perspective view of the surgical suture and suture-needle assembly package of FIG. 4 in the folded condition with the needles exposed;

FIGS. 7 and 8 illustrate the packages of FIGS. 5 and 6, respectively, in the fully closed condition;

FIG. 9 illustrates an alternate embodiment of the package having suture-needle assemblies positioned in the package with the package in the fully unfolded condition;

FIG. 10 illustrates a partial perspective view of the package of FIG. 9 in the folded condition with the needles exposed.

DETAILED DESCRIPTION OF THE PREFERRED EMBODIMENTS

Figure 1:
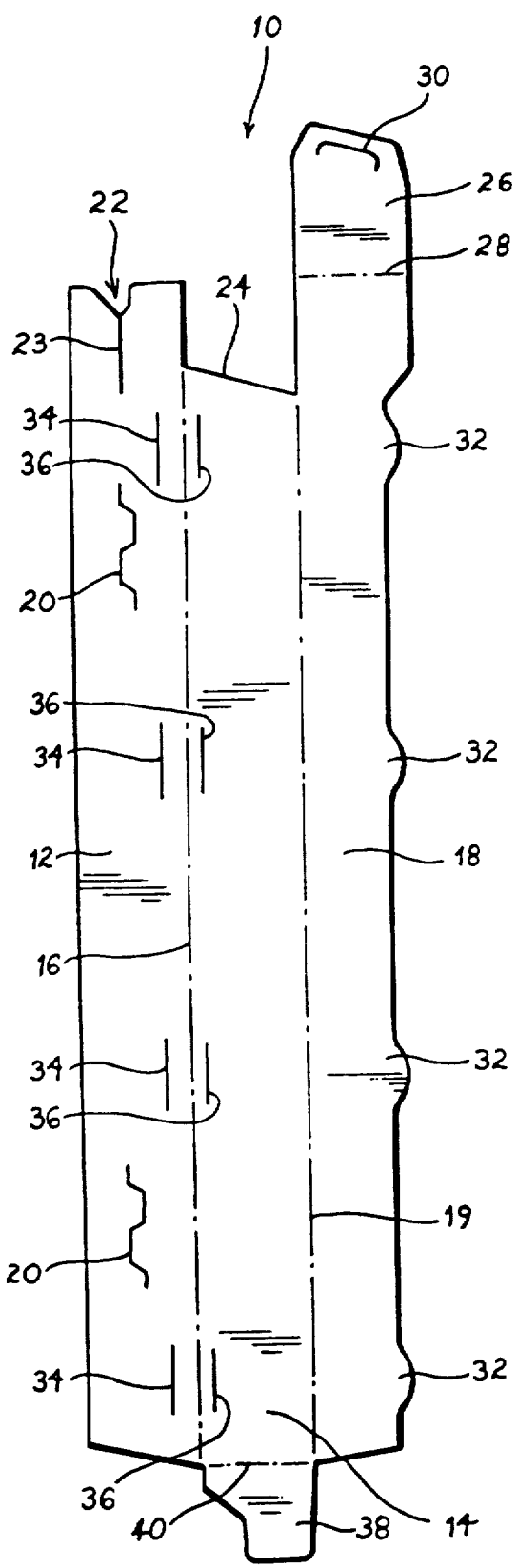
FIG. 1 illustrates a top perspective view of the surgical suture and suture-needle assembly package of the present invention in the unfolded condition.

Referring now in specific detail to the drawings, in which like reference numerals identify similar or identical elements throughout the several views, FIG. 1 shows the package 10 of the present invention in the fully unfolded and unarmed condition. Package 10 essentially comprises a sheet of packaging material, preferably a fibrous material such as paper, paperboard, fiberboard, or Tyvek (a registered trademark of Du-Pont) which is a fibrous material constructed of spun bonded polyolefin fibers which are pressed together to form a sheet of fibrous material. Package 10 consists of a series of interconnected panels, and in the preferred embodiment comprises three panels which are foldable over each other through a series of scored or perforated fold lines.

A first panel 12 serves as a needle and suture retaining panel, and is connected to the second or center panel 14 through a score line 16. When the package is fully folded, center panel 14 forms the front of the package. Panel 14 is connected to third panel 18 through score line 19, and third panel 18 forms the back of the package when the package is in the fully folded condition.

Panel 12 is provided with a series of die cuts 20 which provide a means for retaining the surgical sutures to be packaged within package 10. Panel 12 is further provided with a cutout region 22 and a slit 23 at the top of the package whose function will be described later.

Figure 2:
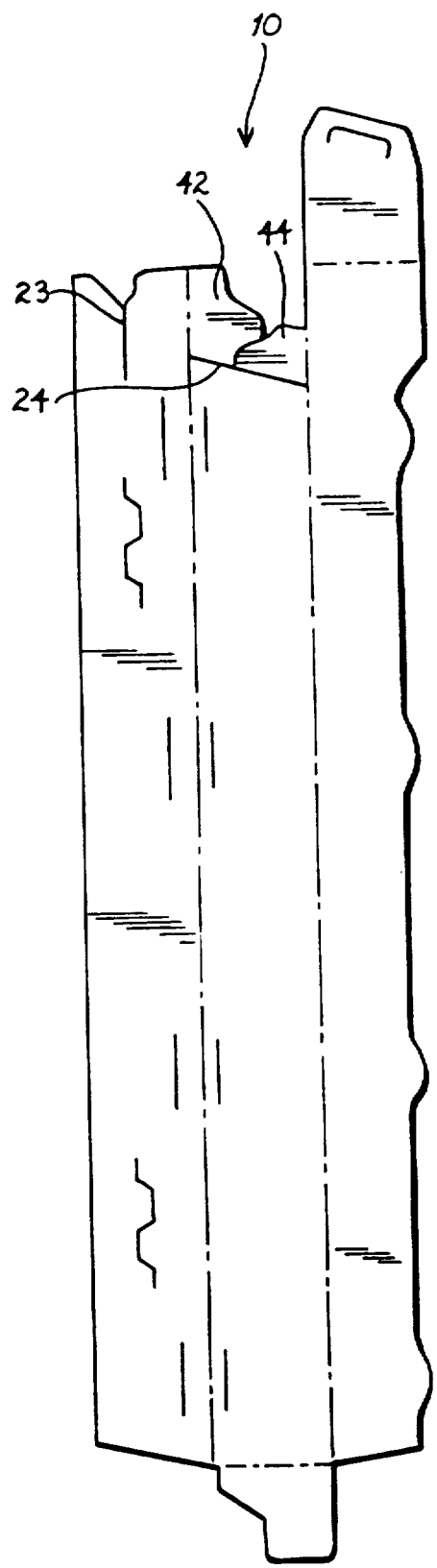
FIG. 2 illustrates an alternate embodiment of the surgical suture and suture-needle assembly package of the present invention in the fully unfolded condition.

Second panel 14 is provided with an end closure flap 38 which extends from the body of the package and is foldable about the second panel 14 through score line 40. Flap 38 provides a bottom closure to the package. In the embodiment of FIG. 1, second panel 14 is provided with an upper edge 24 which defines a needle display area as can best be seen in FIG. 5. In a second embodiment, as shown in FIG. 2, a pair of fold over flaps 42 and 44 provide a cover for the needle display area, and open along score lines 16 and 19 at edge 24. Flaps 42 and 44 are best seen in FIG. 6, wherein flap 42 covers the tips of the needles to further protect the needles within the package.

Figure 11:
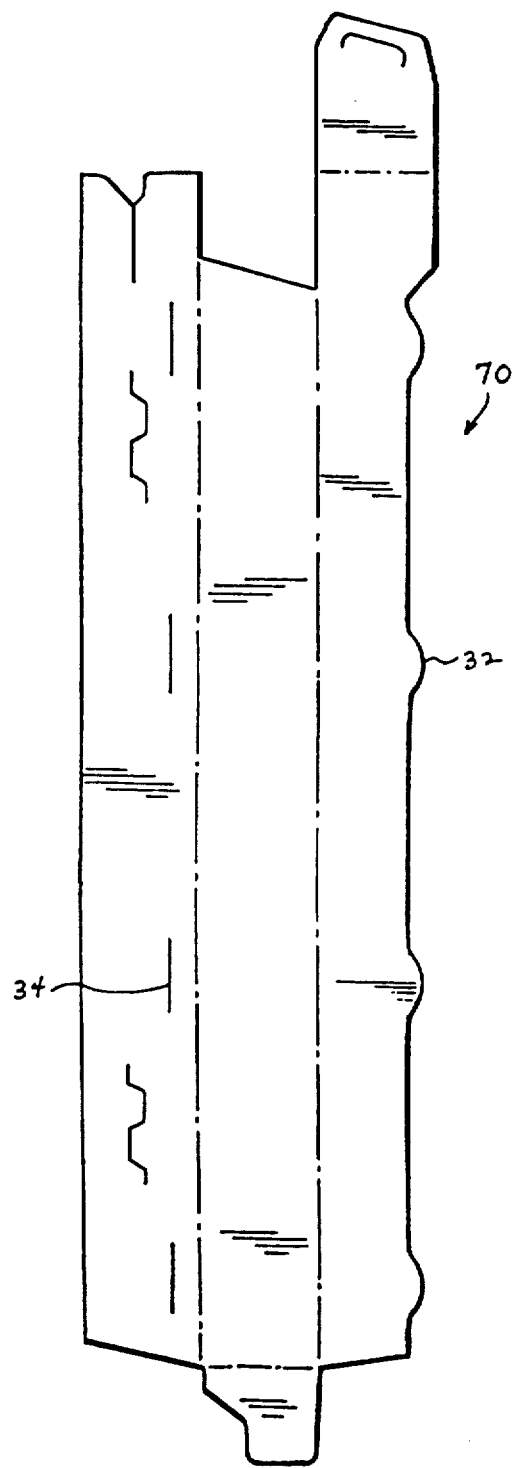
FIGS. 11 and 12 illustrate alternate embodiments of the package of the present invention in the fully unfolded condition.
Figure 12:
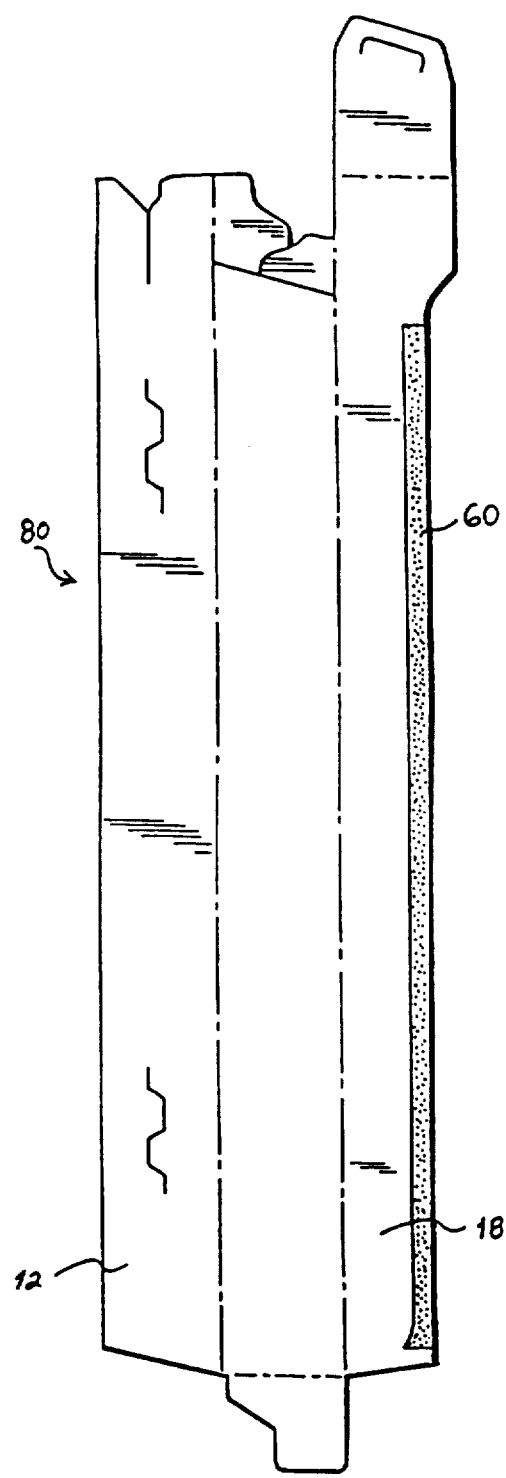

Third panel 18 is provided with a top closure flap 26 which is foldable about score line 28 to provide a cover for the needles when the package is fully folded. Locking tab 30 engages edge 24 of second panel 14 as best seen in FIGS. 7 and 8. Third panel 18 is provided with a series of tabs 32 for engaging slots 34 of first panel 12. The engagement of tabs 32 into slots 34 holds the package in the fully closed position. Tab 32 may be positioned to pass through slot 34 as well as slot 36 on second panel 14 to further secure the package. It is also contemplated that tabs 32 and slots 34 and 36 be eliminated whereby third panel 18 is provided with a strip of adhesive 60, as best seen in FIG. 12, such as a heat or pressure sensitive adhesive material which will secure the third panel 18 to first panel 12 to hold the package in the fully closed position. In addition, slots 36 may be eliminated so that tabs 32 engage only slots 34, as best seen in FIG. 11, to hold the package in the closed position.

Figure 3:
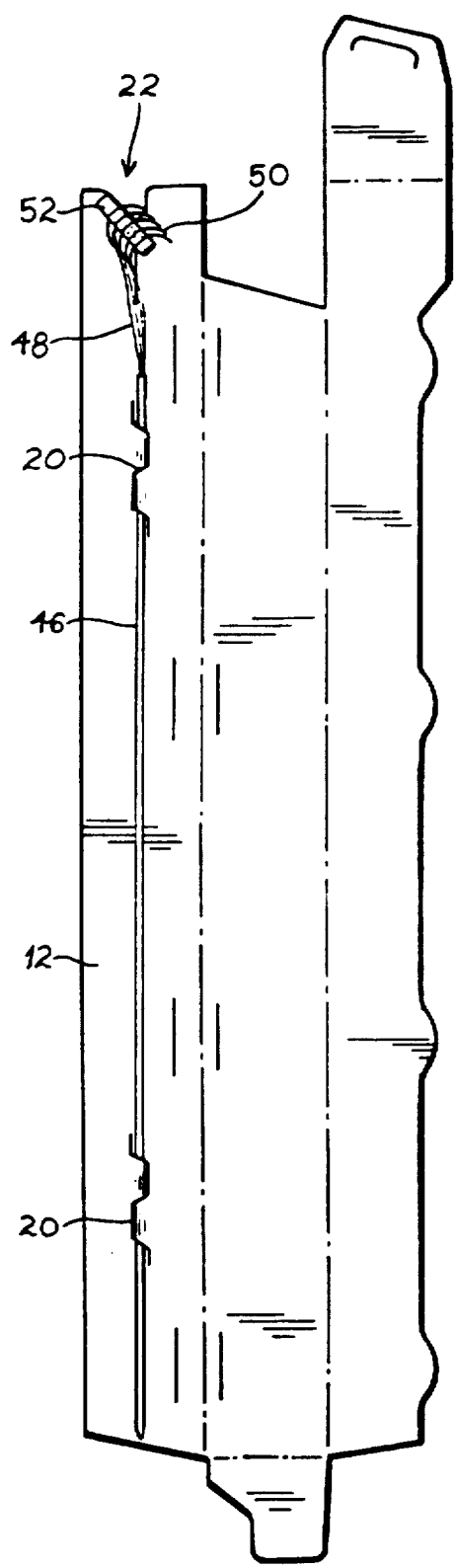
FIG. 3 illustrates the surgical suture and suture-needle assembly package of FIG. 1 having suture-needle assemblies positioned in the package with the package in the fully unfolded condition.

FIG. 3 shows package 10 of FIG. 1 having a number of suture-needle assemblies in position within the package with the package in the fully opened condition. In order to maintain the original shape of sutures 48, the sutures are packaged in a tubular member 46, which is preferably a plastic tube or a tube of rolled paper material which resists bending and folding. Tubular member 46 is held in place by die cuts 20 which provide a means for overlapping tubular member 46 to hold it in place. While any number of die cuts 20 may be provided, the preferred embodiment provides two cuts as seen in FIG. 3. It is also contemplated that die cuts 20 be eliminated and tubular member 46 be secured to first panel 12 through adhesives. In order to secure needles 50, a foam, adhesive-backed needle park 52 is provided which is positioned along an edge of cutout 22. Cutout 22 facilitates grasping of the needles when the package is in the fully folded condition.

Figure 4:
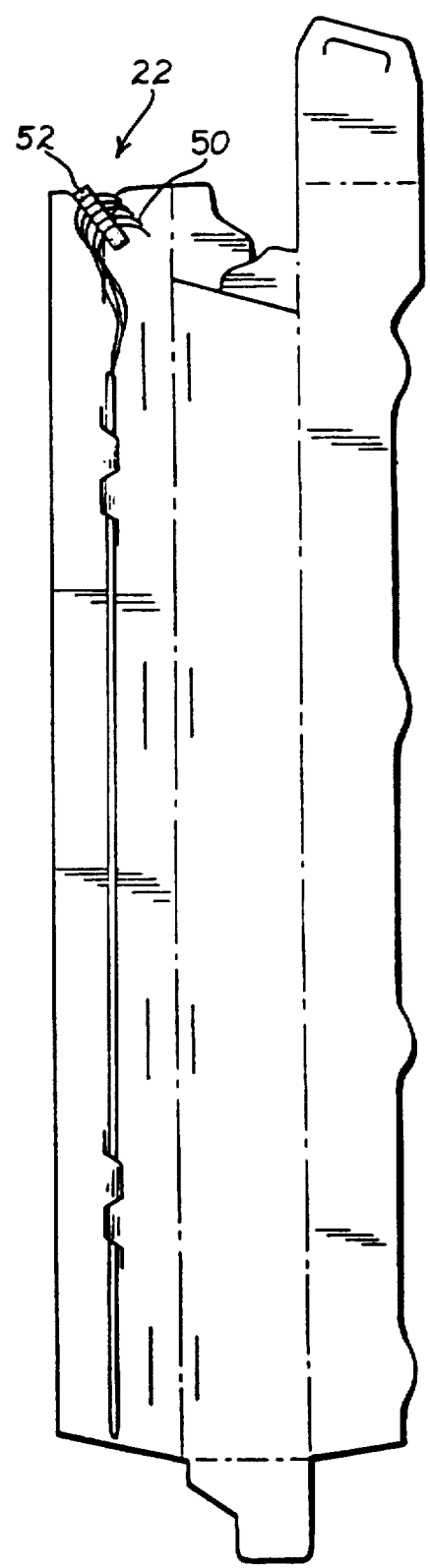
FIG. 4 illustrates the surgical suture and suture-needle assembly package of FIG. 2 having suture-needle assemblies positioned in the package with the package in the fully unfolded condition.

FIG. 4 illustrates an alternate securement means for foam needle park 52 which secures needles 50 at cutout 22. In the embodiment shown in FIG. 4, needle park 52 overlaps cutout 22 so that as panel 12 is folded over panel 14, and panel 18 is folded over panel 12, the adhesive backed needle park 52 may be secured directly to third panel 18 as best seen in FIG. 6.

FIG. 5 shows the package of the present invention in the closed position with the needles 50 secured in foam needle park 52. Needle park 52 is positioned along an edge of gap 22 in first panel 12, and needles 50 are displayed above edge 24 of second panel 14. As seen in FIG. 7, flap 26 is folded along score line 28 so that locking tat, 30 engages edge 24 to close the package about the needles. As best seen in FIGS. 5 and 7, tab 30 is positioned at an angle to scored line 28 which aligns tab 30 with edge 24 in parallel relation when flap 26 is folded over the needles.

FIG. 6 shows needles 50 secured in foam park 52 which overlaps cutout 22 of panel 12. In this manner, the adhesive-backed needle park is secured to both first panel 12 and third panel 18 as shown. Closure flaps 42 and 44 fold over to protect the needle tips and sutures as shown. To close the package, flap 26 is folded along score line 28 so that tab 30 engages edge 24 of second panel 14 in the manner as illustrated in FIG. 8.

FIGS. 9 and 10 show the package of the present invention in which the foam needle park is eliminated and needles 50 and sutures 48 are placed to overlay cutout 22 and slit 23 of panel 12. Tubular member 46 is secured in die-cuts 20 as previously described, and package 10 is folded as described above and as seen in FIG. 10. To secure needles 50, flap 44 is folded over sutures 48, and then flap 42 is folded over needles 50 as shown. The edge of flap 42 is inserted into slit 23 to hold needles 50 in place. Flap 26 is folded over the assembly as described above.

FIGS. 11 and 12 illustrate alternate embodiments of the package of the present invention. Package 70 of FIG. 11 is identical to package 10 of FIG. 1 except that only slots 34 are provided to engage tabs 32. Package 80 of FIG. 12 is identical to package 10 except that the tab and slot arrangement is eliminated and adhesive strip 60 is provided to secure the third panel 18 to first panel 12.

Figure 13:
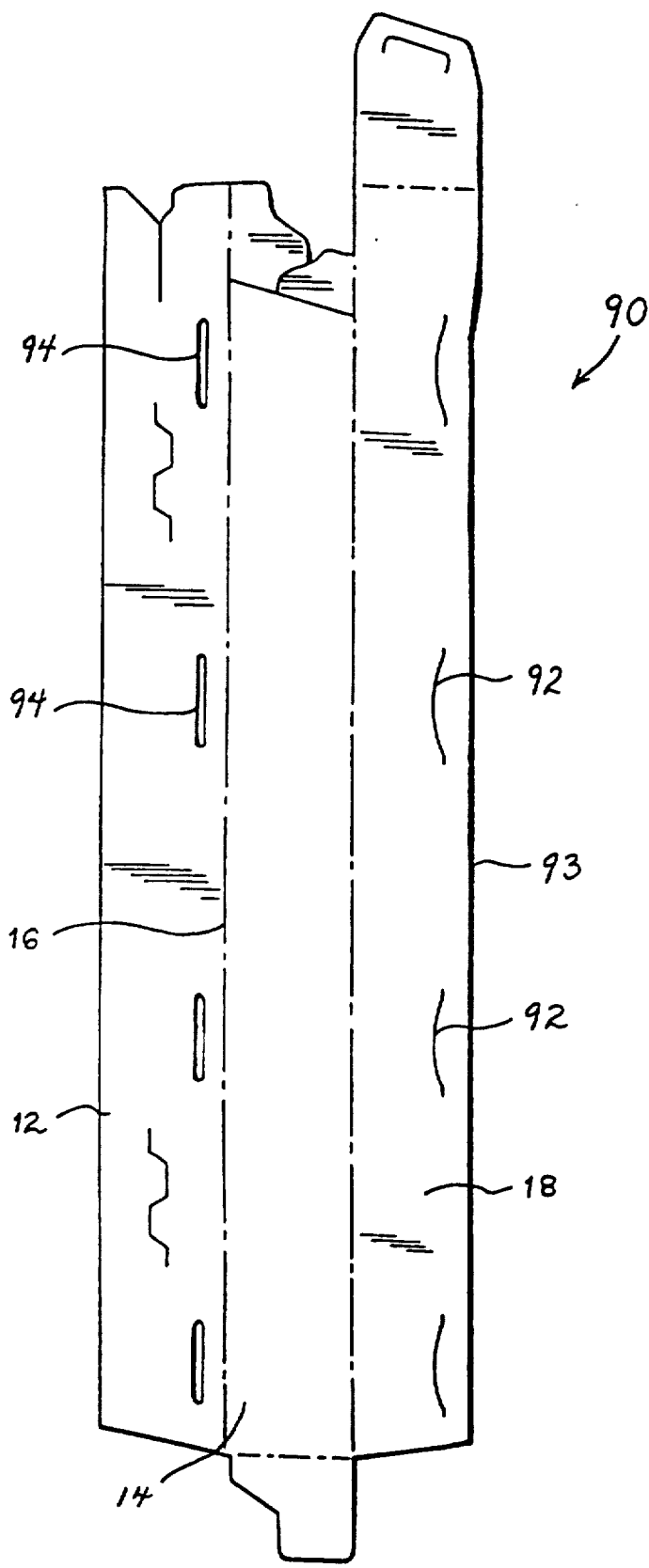
FIG. 13 illustrates a further embodiment of the package of the present invention in the fully unfolded condition.

FIG. 13 illustrates a further, preferred embodiment of the present invention. Package 90 is similar to package 10 except for the provision of inwardly directed tabs 92 which are die-cut into panel 18. Panel 18 accordingly has a straight longitudinal edge 93, which overlaps first panel 12, and if desired, may overlay scored line 16 between panels 12 and 14. Tabs 92 engage openings 94 in panel 12 to hold the package 90 in a folded and closed position.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A package for surgical sutures and suture needle assemblies comprising three interconnected panels, a first panel serving as a suture retaining panel, a second panel connected to said first panel and serving as a front cover, and a third panel connected to said second panel and serving as a back cover, wherein said first panel includes an elongated tubular member for retaining said sutures in said tubular member in an elongated and unfolded condition.

2. A package according to claim 1, wherein said first panel includes means for retaining said tubular member.

3. A package according to claim 2, wherein said means for retaining said tubular member comprises at least one die cut in said panel which is foldable to grasp said tubular member.

4. A package according to claim 2, wherein said means for retaining said tubular member comprises adhesives.

5. A package according to claim 1 wherein said first panel includes means for retaining needles of said suture needle assemblies.

6. A package according to claim 1, wherein said third panel is provided with an extension panel at a first end of said package, said panel being foldable over said package to provide a top for said package, and further including means for securing said panel to said second panel to maintain said package in the closed position.

7. A package according to claim 1, wherein said third panel includes means for holding said package in the fully folded and closed position.

8. A package according to claim 7, wherein said holding means cooperates with at least said first panel to hold said package in the closed position.

9. A package according to claim 7, wherein said holding means comprises at least one tab which interlocks with at least one corresponding slot on said first panel.

10. A package according to claim 9, wherein said at least one tab extends outwardly from a longitudinal edge of said third panel.

11. A package according to claim 9, wherein said at least one tab comprises an inwardly directed die-cut forming an edge which engages said at least one slot on said first panel.

12. A package according to claim 7, wherein said holding means comprises an adhesive strip which secures said third panel to said first panel to hold said package in the closed position.

13. A package according to claim 5, wherein said needle retaining means comprises an adhesive-backed foam needle park, said park being positioned so as to overlap an edge of said first panel to adhere to said third panel when said package is in the closed position.

14. A package according to claim 1, wherein said tubular member comprises a plastic tube.

15. A package for surgical sutures and suture needle assemblies comprising three interconnected panels, a first panel serving as a suture retaining panel, a second panel connected to said first panel and serving as a front cover, and a third panel connected to said second panel and serving as a back cover; and means for retaining said suture in an elongated and unfolded condition in said package positioned on said first panel;

wherein said second panel includes needle display means at a first end of said package, said second panel further including an extension panel at a second end of said package which is foldable over said second panel to provide a bottom for said package.

16. A package according to claim 15, wherein said third panel is provided with an extension panel at a first end of said package, said panel being foldable over said package to provide a top for said package, and further including means for securing said panel to said second panel to maintain said package in the closed position.

17. A package according to claim 15, wherein said needle display means comprises at least one flap member on said second panel which is pivotable away from said needles to display said needles in said package when said package is in a closed position.

18. A package according to claim 17, wherein said flap member engages said first panel to hold said needles of said suture needle assemblies.

19. A package for surgical suture and suture-needle assemblies comprising three interconnected panels, a first panel serving as a suture and needle retaining panel, a second panel connected to said first panel and serving as a front cover, and a third panel connected to said second panel and serving as a back cover, wherein said first panel includes means for holding said suture and needle assemblies in an unfolded condition, said second panel includes needle display means at a first end of said package and a fold over extension panel at a second end of said package, said third panel includes a fold over extension panel at said first end of said package, and said third panel further includes holding means which cooperates with at least said first panel for holding said package in a fully folded and closed position.

20. A package according to claim 19, wherein said means for holding said sutures includes an elongated tubular member for holding said sutures therein in an elongated and unfolded condition.

21. A package according to claim 20, wherein said tubular member is secured to said first panel by engagement with a series of die cuts in said first panel which grasp said tubular member.

22. A package according to claim 19, wherein said holding means on said third panel comprises a series of tabs which engage corresponding slots on at least said first panel to hold said package closed.

23. A package according to claim 22, wherein said series of tabs extend outwardly from a longitudinal edge of said third panel to engage said slots on said first panel.

24. A package according to claim 22, wherein said series of tabs comprise a series of inwardly directed die-cuts forming edges which engage said slots on said first panel.

25. A package according to claim 19, wherein said holding means comprises a strip of adhesive material on said third panel which engages said first panel to hold said package closed.

26. A package according to claim 19, wherein said first panel includes means for securing needles of said suture needle assemblies.

27. A package according to claim 19, wherein said needle display means comprises a pair of flaps which fold away from said second panel to display said needles.

28. A package according to claim 19, wherein said needle display means comprises a flap member which engages a slit in said first panel to hold said needles in place.

29. A method of loading sutures into a surgical suture package, said package having three interconnected panels joined by longitudinal scored lines, said method comprising:
placing at least one suture in an elongated tubular member;
securing said tubular member to a first panel of said package;
folding said first panel having said tubular member containing said at least one suture over a second panel of said package;
folding a third panel over said first panel; and
securing said third panel to said first panel to maintain said package in a fully folded and closed condition.

30. A method according to claim 29, wherein said second panel further includes a flap member, said method further comprising the step of folding said flap member over said first panel after said first panel is folded over said second panel.

31. A method according to claim 29, wherein said third panel includes a flap member, said method further including the step of folding said flap member over said second and first panel and securing said flap to said second panel after said third panel is folded over said first panel and secured thereto.

32. A method according to claim 29, wherein said step of securing said tubular member to said first panel comprises positioning said tubular member within a plurality of overlapping die-cut flaps to secure said tubular member.

33. A method according to claim 29, wherein a plurality of sutures are positioned in said tubular member, said sutures having needles attached to one end, said method further comprising the step of securing said needles to said package after said tubular member is secured to said first panel.

34. A method according to claim 29, wherein said needles are secured to a foam needle retaining member which is secured to said first panel.

35. A method according to claim 33, wherein said second panel includes at least one pivotable flap member adjacent said needles, said method further comprising folding said flap member over said needles and securing said flap member in a slot in said first panel to secure said needles to said package.

36. A method for packaging surgical suture-needle assemblies, said package including three interconnected panels, a first panel serving as a suture and needle retaining panel, a second panel connected to said first panel and serving as a front cover, and a third panel connected to said second panel and serving as a back cover, said first panel including a tubular member for holding said suture and needle assemblies in an unfolded condition, said second panel including needle display means at a first end of said package and a fold over extension panel at a second end of said package, said third panel including a fold over extension panel at said first end of said package, and said third panel further including holding means which cooperates with at least said first panel for holding said package in a fully folded and closed position, said method comprising:
placing at least one suture-needle assembly in said elongated tubular member;
securing said elongated tubular member to said first panel;
securing said needles to said first panel;
folding said first panel over said second panel;
folding said second panel fold over extension panel over said first panel;
folding said third panel over said first panel;
securing said third panel to at least said first panel to maintain said package in a closed condition; and
folding said third panel fold over extension panel over said first and second panel and securing said extension panel to said second panel to fully close said package.

37. A method according to claim 36, wherein said step of securing said needles to said first panel comprises positioning said needles in a foam needle park secured to said first panel.

38. A method according to claim 36, wherein said needle display means includes at least one flap member pivotable from said second panel, said method further comprising the step of folding said flap member over said needles and engaging said flap member in a slot in said first panel to secure said needles to said first panel.

39. A method of removing a surgical suture-needle assembly from a package, said package including three interconnected panels, a first panel having said suture needle assembly secured thereto in an elongated tubular member, said needle assembly being secured in a foam needle park on said first panel, said first panel being folded over a second panel, said second panel having at least one flap member forming needle display means at a first end and an extension panel folded over said first panel at a second end, and a third panel folded over said first panel and secured thereto to maintain said package in a fully closed position, said third panel including a fold over extension panel at said first end which is folded over said first and second panels and secured to said second panel; said method comprising:

opening said package by unfolding said third panel extension panel to reveal said needle display means;

unfolding said flap member of said needle display means to reveal said needle;

grasping said needle; and removing said suture-needle assembly from said package by sliding said assembly out of said elongated tubular member;

wherein said suture is maintained in an unfolded condition by said tubular member.

* * * * *

UNITED STATES PATENT AND TRADEMARK OFFICE
CERTIFICATE OF CORRECTION

PATENT NO. : 5,127,518

DATED : July 7, 1992

INVENTOR(S) : Henry A. Holzwarth et al.

It is certified that error appears in the above-identified patent and that said Letters Patent is hereby corrected as shown below:

| | |
|---|---|
| Column 2, line 46 | "secured to &:he" should be --secured to the-- |
| Column 4, line 34 | "!8" should be --18-- |
| Column 5, line 12 | "locking tat" should be --locking tab-- |

Signed and Sealed this

Tenth Day of August, 1993

Attest:

MICHAEL K. KIRK

Attesting Officer

Acting Commissioner of Patents and Trademarks